United States Patent [19]

Kasama et al.

[11] Patent Number: 5,093,339
[45] Date of Patent: Mar. 3, 1992

[54] PYRANO[F]QUINOLINE DERIVATIVES AND PHARMACEUTICAL COMPOSITIONS CONTAINING THE SAME

[75] Inventors: Toshio Kasama, Toshima; Kiyoshi Mayuzumi, Matsudo; Ryuji Monden, Misato; Kenji Tamaru, Matsudo, all of Japan

[73] Assignee: Kodama Kabushiki Kaisha, Tokyo, Japan

[21] Appl. No.: 393,271

[22] Filed: Aug. 14, 1989

[30] Foreign Application Priority Data

Aug. 16, 1988 [JP] Japan .................. 63-203439

[51] Int. Cl.$^5$ .................. C07D 491/06; A61K 31/44
[52] U.S. Cl. .................. 514/291; 514/381; 546/89; 548/250
[58] Field of Search .................. 546/89; 548/250; 514/291, 381

[56] References Cited

FOREIGN PATENT DOCUMENTS 2035312A 6/1980 United Kingdom .

OTHER PUBLICATIONS

Otsuka Pharm. Co., "Carbostyril Derivatives", CA 98:143287h (1983).
Takao et al., "Studies of 2-Oroquinoline . . . ", CA 103:141893a (1985).

*Primary Examiner*—C. Warren Ivy
*Assistant Examiner*—Celia Chang
*Attorney, Agent, or Firm*—Oliff & Berridge

[57] ABSTRACT

Pyrano[f]quinoline derivatives of the formula (I):

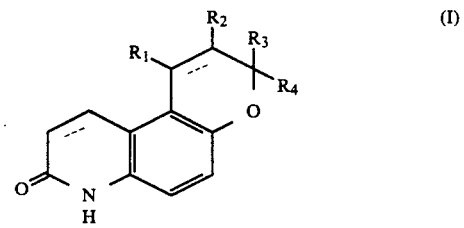

wherein $R_1$ and $R_2$ represent hydrogen, hydroxyl group or a group of the formula:

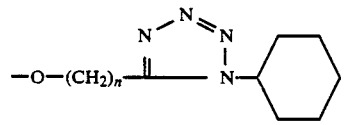

wherein n represents an integer from 1 to 4, $R_3$ and $R_4$ represent hydrogen or a lower alkyl group, and the broken lines in the rings represent that the bond between the carbon atoms at the 1- and 2-positions and the bond between the carbon atoms at the 9- and 10-positions may be double bonds, and pharmaceutical compositions containing the derivatives. The derivatives and compositions are useful as anti-thrombotic agents; cerebral circulation improving agents, hypotensive agents, anti-angina agents, anti-asthmatic agents, anti-ulcer agents and anti-PAF agents.

3 Claims, No Drawings

PYRANO[F]QUINOLINE DERIVATIVES AND PHARMACEUTICAL COMPOSITIONS CONTAINING THE SAME

BACKGROUND OF THE INVENTION

Field of the Invention

The present invention relates to novel pyranoquinoline derivatives and pharmaceutical compositions containing the derivatives as an effective component.

SUMMARY OF THE INVENTION

More specifically, the novel pyranoquinoline derivatives according to the present invention are represented by the formula (I):

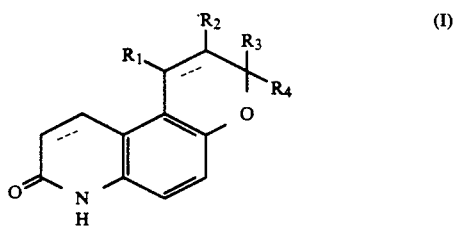

wherein, $R_1$ and $R_2$ are identical or different and represent hydrogen, hydroxyl group or a group of the formula:

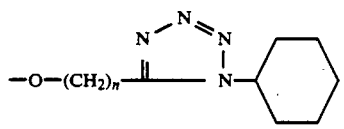

wherein, n represents an integer from 1 to 4, $R_3$ and $R_4$ are identical or different and represent hydrogen or a lower alkyl group, and the broken lines in the rings represent that the bond between the carbon atoms at the 1- and 2-positions and the bond between the carbon atoms at the 9- and 10-positions may be double bonds; excluding the compounds of the formula (I), wherein $R_1$ and $R_2$ are hydrogen, $R_3$ and $R_4$ are identical or different and represent a lower alkyl, and the bond between the carbon atoms at the 1- and 2-positions and the bond between the carbon atoms at the 9- and 10-positions are both double bonds.

DETAILED DESCRIPTION OF THE INVENTION

The present inventors have found, after extensive research, that the compounds of the formula (I) have platelet aggregation inhibitory action, phosphodiesterase inhibitory action, blood-flow increasing action and blood pressure reducing action and are useful as anti-thrombotic agents, cerebral circulation improving agents, hypotensive agents, anti-angina agents, anti-asthmatic agents, anti-ulcer agents and anti-PAF agents.

In the formula (I), lower alkyl groups $R_3$ and $R_4$ include straight chain alkyl groups such as, for example, methyl, ethyl, propyl, butyl, etc. and branched chain alkyl groups such as isopropyl, isobutyl, tert.-butyl, etc.

The compounds of the present invention can be produced by various methods and specifically by the method based on the following reaction sequences:

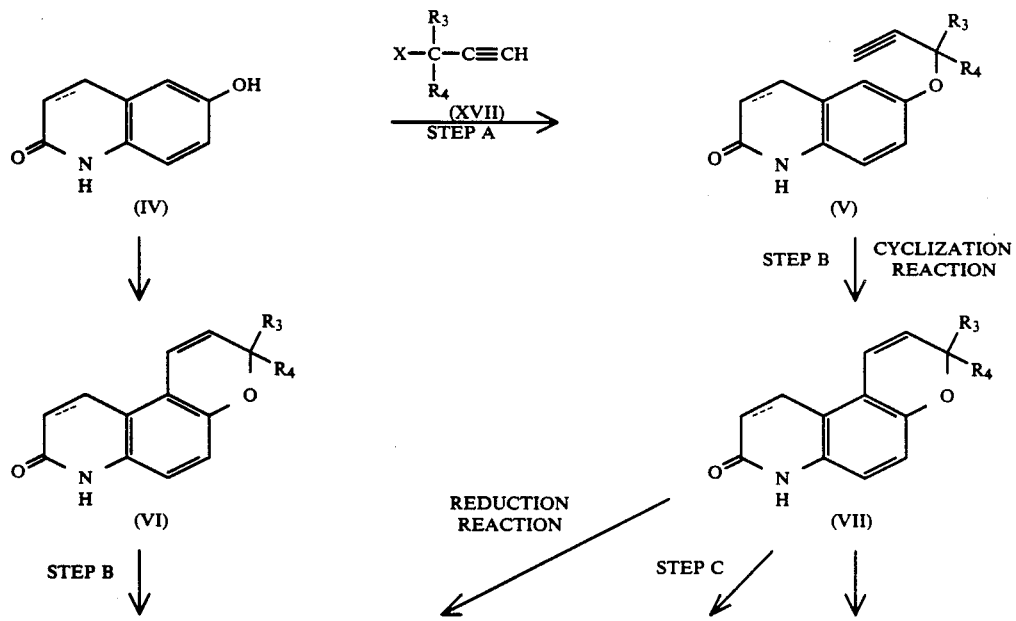

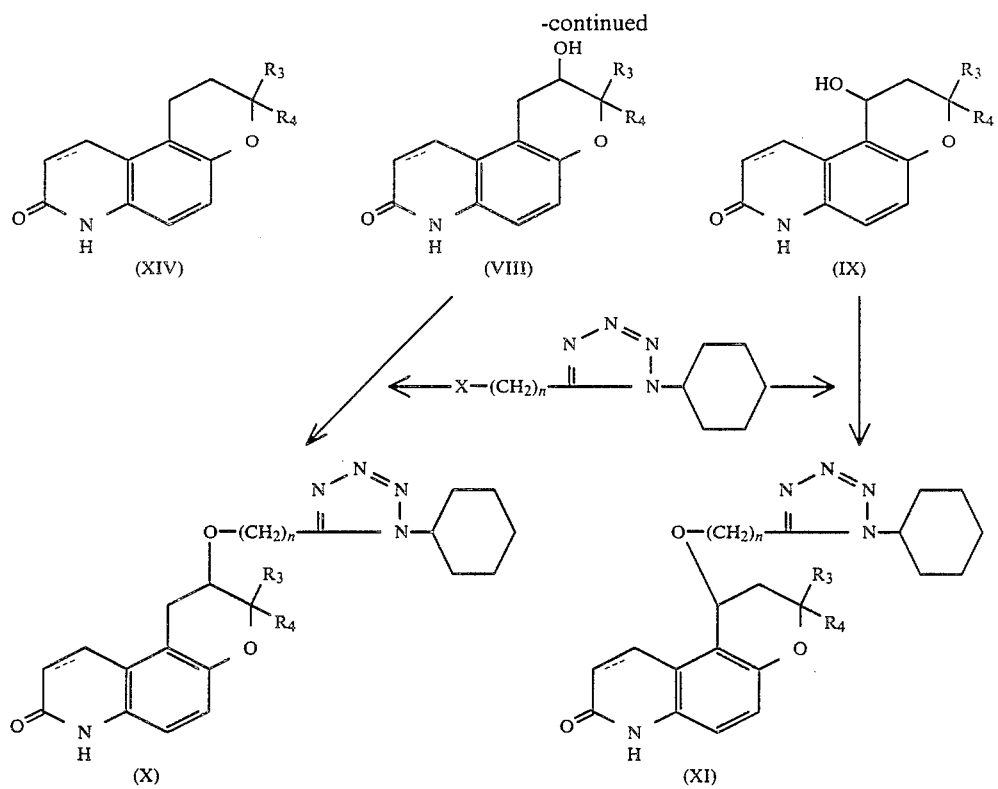

wherein, R₃ and R₄ are as defined in the above and X represents a halogen atom.

Namely, the present compounds can be prepared according to the following methods. 1. Process for preparation of pyrano[f]quinoline compounds (1) In this process, a starting material, i.e., a known compound 6-hydroxy-1H-quinoline-2-one or 6-hydroxy-3,4-dihydro-(1H)-quinoline-2-one of the formula (IV), and a halogenated acetylene derivative are subjected to dehydrohalogenation according to a conventional method to give a 6-(2-propenyloxy) quinoline-2-one derivative of the formula (V), and the resulting compound (V) is subjected to cyclization reaction according to a conventional method to give a compound of the formula (VII). (Steps A, B)

The compounds of the formula (VII) correspond to those of the formula (I) wherein $R_1$ and $R_2$ represent hydrogen and the bond between the carbon atoms at the 9- and 10-positions is a double bond.

The halogen atom X in the halogenated acetylene derivative of the formula (XVII) used in Step A includes bromine, chlorine and iodine atoms.

The dehydrohalogenation reaction is carried out by using a basic compound as a dehalogenating agent. Such basic compounds include known inorganic bases such as sodium hydroxide, potassium hydroxide, sodium carbonate, potassium carbonate, and sodium hydrogencarbonate, as well as organic bases such as sodium methylate, sodium ethylate, pyridine, triethylamine and N,N-dimethylaniline.

The dehydrohalogenation reaction is advantageously carried out in the presence of a metal iodide such as sodium iodide or potassium iodide.

(2) Preparation of 1,2-dihydropyranoquinoline (i) The compounds of the formula (XIV), wherein the bond between the carbon atoms at the 9- and 10-positions is a single bond, can be readily produced by subjecting the compounds of the formula (VII) to a conventional catalytic reduction reaction.

As the catalysts therefor can be used palladium carbon (Pd/C), Raney nickel, platinum carbon, rhodium or the like. The reaction proceeds under normal pressure or pressurization.

(ii) The compounds of the formula (XIV) can also be obtained by subjecting halogenated alkene derivatives and the starting compounds of the formula (IV) to dehydrohalogenation to give the compounds of the formula (VI) and then subjecting the resulting compounds of the formula (VI) to a cyclization reaction similarly as in the process (I).

(3) Preparation of hydroxypyranoquinoline

The compounds (VIII) and (IX), which correspond to the compounds (I) wherein $R_1$ or $R_2$ is hydroxyl group, can be obtained by subjecting the compounds (VII) to a hydroboration oxidation reaction.

The reagents used in the hydroboration oxidation reaction include borane complex salts such as borane-tetrahydrofuran complex salt, borane-pyridine complex salt, borane-dimethylamine complex salt and borane-triethylamine complex salt. The oxidizing agents therefor include a basic hydrogen peroxide.

(4) Preparation of pyranoquinolinone alkyl 1-cyclohexyl tetrazole

The compounds of the formulae (X) and (XI) can be produced by subjecting the compounds of the formula (VIII) or the formula (IX) and (1-cyclohexyltetrazole-5-yl) halogenated alkyl compounds to a dehydrohalogenation reaction.

Representative compounds of the present invention include the compounds illustrated in the following examples, which are not to restrict the present invention.
3-methyl-1,2-dihydro-3H-pyrano[3,2-f]quinoline-8(7H)-one 3,3-dimethyl-1,2-dihydro-3H-pyrano[3,2-f]quinoline-8(7H)-one
3,3-dimethyl-1,2,9,10-tetrahydro-3H-pyrano[3,2-f]quinoline-8(7H)-one
3,3-dihydro-3H-pyrano[3,2-f]quinoline-8(7H)-one
1,2,3,3-tetrahydro-3H-pyrano[3,2-f]quinoline-8(7H)-one
2-hydroxy-1,2,3,3-tetrahydro-3H-pyrano[3,2-f]quinoline-8(7H)-one
3,3-dimethy-2-hydroxy-1,2-dihydro-3H-pyrano[3,2-f]quinoline- 8(7H)-one
1-hydroxy-1,2,3,3-tetrahydro-3H-pyrano[3,2-f]quinoline-8(7H)-one
3,3-dimethyl-1-hydroxy-3H-pyrano[3,2-f]quinoline-8(7H)-one
2-(1-cyclohexyltetrazole-5-ylmethoxy)-3,3-dimethyl-1,2-dihydro-3H-pyrano[3,2-f]quinoline-8(7H)-one
3-ethyl-1,2-dihydro-3H-pyrano[3,2-f]quinolineine-8(7H)-one
2-hydroxy-1,2,3,3,9,10-hexahydro-3H-pyrano[3,2-f]quinoline-8(7H)-one
2-[4-(1-cyclohexyltetrazole-5-yl)butyoxy]-1,2,3,3,-tetrahydro-3H-pyrano[3,2-f]quinoline-8(7H)-one
3,3-dimethyl-3H-pyrano[3,2-f]quinoline-8(7H)-one (boiling point: 320° C.)
1,2,3,3,9,10-hexahydro-3H-pyrano[3,2-f]quinoline-8(7H)-one (boiling point: 200° C.)

The compounds of the formula (I) according to the present invention inhibit platelet aggregation reaction realised by various agents, possess vasodilatation action, blood-flow increasing action, pulse increasing action and anti-PAF action, and are useful as novel anti-thrombotic agents, cerebral circulation improving agents, hypotensive agents, anti-angina agents, anti-asthmatic agents and anti-ulcer agents.

Toxicity of the present compounds is very low. Toxic dosage of the compounds is not less than 1500 mg when orally administered to a mouse. Thus, it is presumed that the compounds would be quite safe as medical drugs.

With respect to administration, it is suitable to administer orally a dose of 1 to 200 mg one to three times per day, or intrarectally a dose of 1 to 200 mg one to three times per day, or intravenously a dose of 0.1 to 20 mg one to three times per day.

The form of the drug can be optional. One or two or more of the compounds selected from those according to the present invention are mixed together with carriers, excipients and other additives conventionally used for drugs to give a formulation and the resulting formulation can be provided in a desired form such as powders, granules, tablets, capsules, syrups, injection liquids, ointments, or creams.

As the carriers, excipients and other additives which are conventionally used can be employed.

The present invention will be explained in detail by way of the following examples.

1. Preparation of the present compounds

PREPARATION EXAMPLE 1

Preparation of
3-methyl-1,2-dihydro-3H-pyrano[3,2-f]quinoline-8(7H)-one 6-hydroxyquinoline-2-one (481 mg) and orthophosphoric acid (0.55 ml) were dissolved in 5 ml of benzene, and thereto was added dropwise with stirring 297 mg of butadiene dissolved in 5 ml of benzene. The resulting mixture was heated under reflux at 80° C. for 12 hours. The reaction liquid was poured into ice-cold water and extracted with 100 ml of ethyl acetate. The extracted liquor was washed with water and the ethyl acetate solution was dehydrated by addition of anhydrous sodium sulfate and filtered. The solvent in the filtrate was distilled away under reduced pressure. The resulting residue was recrystallized from ethanol to give 224 mg of white needle-like crystals.

melting point: 267°-269° C.
NMR$\delta$: 1.43 (3H, d, J=6.35Hz, —$CH_3$), 1.81 (1H, m, —$CH_2$—),
2.11 (1H, m, —$CH_2$—), 2.99 (2H, m, —$CH_2$—),
4.13 (1H, m, —CH—),
6.74 (1H, d, J=9.28Hz, benzene ring),
7.05 (1H, d, J=8.79Hz, benzene ring),
7.24 (1H, d, J=8.79Hz, benzene ring),
7.91 (1H, d, J=9.28Hz, benzene ring)

PREPARATION EXAMPLE 2

Preparation of
3,3-dimethyl-1,2-dihydro-3H-pyrano[3,2-f]quinoline-8(7H)-one 6-hydroxyquinoline-2-one (481 mg) and orthophosphoric acid (0.55 ml) were dissolved in 5 ml of benzene, and then a solution of 0.55 ml of isoprene in 5 ml of benzene was added thereto with stirring. The resulting mixture was heated under reflux for 30 minutes. The reaction liquid was poured into ice-cold water and extracted with ethyl acetate. The extracted liquor was washed with water, dehydrated by addition of anhydrous sodium sulfate and filtered. The solvent in the filtrate was distilled away under reduced pressure, and the resulting residue was recrystallized from ethanol to give 567 mg of pale yellow needle-like crystals.

melting point: 250°-252° C.
NMR$\delta$: 1.35 (6H, S, $CH_3$—), 1.91 (2H, t, J=6.83Hz, —$CH_2$—),
2.95 (2H. t. J=6.83Hz, —$CH_2$—),
6.75 (1H, d, J=9.86Hz, benzene ring H),
7.03 (1H, d, J=8.85Hz, benzene ring H),
7.26 (1H, d, J=8.85Hz, benzene ring H),
7.94 (1H, d, J=9.86Hz, benzene ring H),
12.57 (1H, br, —NH—)

PREPARATION EXAMPLE 3

Preparation of
3,3-dimethyl-1,2,9,10-tetrahydro-3H-pyrano[3,2-f]quinoline-8(7H)-one The compound (500 mg) obtained in Preparation Example 2 was dissolved in 35 ml of ethanol, incorporated with 400 mg of palladium carbon and then subjected to hydrogenation reaction at 70° to 80° C. under 20 atm. for 5 hours. The reaction liquid was filtered and the solvent in the filtrate was distilled away under reduced pressure. The resulting residue was recrystallized from ethanol to give 433 mg of white needle-like crystals.

melting point: 200°-205° C.
NMR$\delta$: 1.32 (6H, s, —$CH_3$),
1.83 (2H, d, J=6.84Hz, —$CH_2$—),
2.55-2.70 (6H, m, —$CH_2$—),
2.85 (2H, m, —$CH_2$—),
6.61 (2H, d, J=8.55Hz, benzene ring H)

PREPARATION EXAMPLE 4

Preparation of
3,3-dihydro-3H-pyrano[3,2-f]quinoline-8(7H)-one 6-propoxyquinoline-2-one (1.7 g) was dissolved in 200 ml of diethyl-aniline and the resulting solution was heated with stirring under reflux for 3 hours. The reaction liquid was poured into an ice-cooled 20% hydrochloric acid solution to precipitate crystals. The crystals were recrystallized from methanol to give 697 mg of white needle-like crystals.

melting point (m.p.): 254°–256° C.
NMRδ: 4.79 (2H, dd, J=3.90Hz, 1.47Hz, —CH$_2$—),
6.02 (1H, m, —CH=),
6.63 (1H, d, J=9.77Hz, benzene ring H),
6.92 (1H, d, J=10.25Hz, benzene ring H),
6.97 (1H, d, J=8.79Hz, benzene ring H),
7.17 (1H, d, J=8.79Hz, benzene ring H),
7.94 (1H, d, J=9.77Hz, benzene ring H),
11.78 (1H, m, —NH—)

PREPARATION EXAMPLE 5

Preparation of 1,2,3,3-tetrahydro-3H-pyrano-[3,2-f]quinoline-8(7H)-one

The compound (80 mg) obtained in Preparation Example 4 was dissolved in 10 mg of ethanol, incorporated with 80 mg of 10% palladium carbon and then subjected to hydrogenation reaction at room temperature for one hour. The reaction liquid was filtered and the solvent in the filtrate was distilled away under reduced pressure. The residue was recrystallized from ethanol to give 63 mg of white needle-like crystals.

melting point: 288°–290° C.
NMRδ: 2.11 (2H, m, —CH$_2$—),
2.94 (2H, m, —CH$_2$—),
4.18 (2H, m, —CH$_2$—),
6.63 (1H, d, J=9.77Hz, aromatic ring H),
6.96 (1H, d, J=9.28Hz, aromatic ring H),
7.15 (1H, d, J=9.28Hz, aromatic ring H),
7.85 (1H, d, J=9.77Hz, aromatic ring H),
11.59 (1H, m, —NH—)

PREPARATION EXAMPLE 6

Preparation of 2-hydroxy-1,2,3,3-tetrahydro-3H-pyrano[3,2-f]quinoline-8(7H)-one

The compound (114 mg) obtained in Preparation Example 4 was dissolved in 4 ml of tetrahydrofuran and 52 mg of sodium boron hydride was added thereto. To the resulting solution was added dropwise gradually with stirring at room temperature a solution of 265 mg of boron trifluoride in ether. After addition, the reaction liquid was stirred for 3 hours and then incorporated with water until bubbling in the liquid was terminated. The reaction liquid was then made with a 10% sodium hydroxide solution and then gradually incorporated with 0.2 ml of aqueous hydrogen peroxide. After stirring at 50° C. for one hour, the reaction liquid was neutralized with a 10% hydrochloric acid solution and extracted with ethyl acetate. The extracted liquor was washed with water, dehydrated by addition of anhydrous sodium sulfate and then concentrated. The resulting concentrate was subjected to column chromatography (on silica gel, eluting with n-hexane/ethyl acetate (1:1)) to give 8.35 mg of white needle-like crystals.

melting point: 265°–267° C.
NMR (CDCl$_3$): 2.79 (2H, d, J=709, —CH$_2$—),
3.08 (2H, d, J=709, —CH$_2$—),
3.08 (1H, m, ON),
4.11 (1H, m, —CH—),
6.55 (1H, d, J=9.76Hz, benzene ring moisture),
7.10 (1H, d, J=8.28Hz, benzene ring moisture),
7.12 (1H, d, J=8.28Hz, benzene ring moisture),
7.97 (1H, d, J=9.76Hz, benzene ring moisture),
11.45 (1H, m, —NH—)

PREPARATION EXAMPLE 7

Preparation of 3,3-dimethyl-1,2-hydroxy-1,2-dihydro-3 H-pyrano[3,2-f]quinoline-8(7H)-one In 400 ml of tetrahydrofuran was dissolved 11.35 g of 3,3-dimethyl-3H-pyrano[3,2-f]quinoline-8(7H)-one, and then the procedures in Preparation Example 6 were repeated to give 948 mg of white needle-like crystals.

melting point: 275°–278° C.
NMR (CDCl$_3$)δ: 1.29 (3H, s, CH$_3$—),
1.35 (3H, s, CH —),
2.86 (1H, dd, J=6.84Hz, 7.09Hz, —CH$_2$—),
3.15 (1H, dd, J=6.86Hz, 5.37Hz, —CH$_2$—),
3.43 (1H, m, —OH),
3.86 (1H, m, —CH—),
6.61 (1H, d, J=9.75Hz, benzene ring moiety),
6.97 (1H, d, J=8.79Hz, benzene ring moiety),
7.12 (1H, d, J=8.79Hz, benzene ring moiety),
7.80 (1H, d, J=9.75Hz, benzene ring moiety)

PREPARATION EXAMPLE 8

Preparation of
1-hydroxy-1,2,3,3-tetrahydro-3H-pyrano[3,2-f]quinoline-8(7H)-one

Similarly to the procedures in Preparation Example 6, there is obtained 6 mg of white needle-like crystals.

PREPARATION EXAMPLE 9

Preparation of 3,3-dimethyl-1-hydroxy-3H-pyrano [3,2-f]quinoline-8(7H)-one

Similarly to the procedures in Preparation Example 7, there was obtained 845 mg of white needle-like crystals.

PREPARATION EXAMPLE 10

Preparation of 2-(1-cyclohexytetrazole-5-ylmethoxy)-3,3-dimethyl-1,2-dihydro-3H-pyrano[3,2-f]quinoline-8(7H)-one The compound (324 mg) obtained in Preparation Example 7 and potassium hydroxide (425 mg) were dissolved in 15 ml of isopropanol and the resulting solution was refluxed for one hour. To this solution was added dropwise a solution of 489 mg of (1-cyclohexyltetrazole-5-yl) methyl chloride in 10 ml of isopropanol, and the resulting mixture was refluxed at 90° to 100 ° C. with stirring. After completion of the reaction, the reaction liquid was poured into ice-cold water and extracted with ethyl acetate. The extracted liquor was washed with a 10% sodium hydroxide solution and then with a 10% hydrochloric acid solution to neutralize it. The extracted liquor was further washed several times with water, dehydrated with anhydrous sodium sulfate and then filtered. The filtrate was distilled away under reduced pressure and the resulting residue was subjected to column chromatography (on silica gel, eluting with ethyl acetate) to give 10 mg of yellow needle-like crystals. melting point: 250°–252° C.

NMR (CDCl$_3$)δ: 1.29 (3H, s, —CH$_3$),
1.36 (3H, s, —CH$_3$), 2.09 (2H, s, —CH$_2$—O),
0.70–2.10 (10H, m,

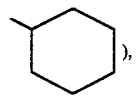
), 2.96 (1H, dd, J=5.13Hz, 7.33Hz, —CH$_2$—),
3.29 (1H, dd, J=5.37Hz, 7.33Hz, —CH$_2$—),
5.12 (1H, t, J=5.13Hz, 5.37Hz,

), 6.74 (1H, d, J=9.76Hz, benzene ring moiety),
7.08 (1H, d, J=8.79Hz, benzene ring moiety),
7.22 (1H, d, J=8.79Hz, benzene ring moiety),
7.84 (1H, d, J=9.76Hz, benzene ring moiety),
11.70 (1H, m, —NH—)

2. Pharmacological Test

The compounds obtained in the above preparation examples were evaluated as to effectiveness.

TEST EXAMPLE 1

Platelet aggregation inhibitory action

For evaluating the platelet aggregation inhibitory action of the present compounds, platelet plasma containing $5 \times 10^5$ of platelets in 1 μl of plasma was prepared by appropriately mixing platelet-rich plasma (PRP) of rabbit with platelet-poor plasma (PPP). By using the platelet plasma, the present compounds were measured on 50% inhibitory efficacy (IC 50) against each of platelet aggregation accelerators, 10 μM of adenosine diphosphate (ADP), 0.01 μg/ml of platelet activation factor (PAF), 300 μM of arachidonic acid (AA) and 30 μg/ml of collagen. The results thereof are shown in Table 1.

TABLE 1

| Compound | Coagulant (ID50 mμ) | | | |
|---|---|---|---|---|
|  | ADP | PAF | AA | Collagen |
| Preparation Example 1 | 0.005 | 0.008 | 0.003 | 0.005 |
| Preparation Example 2 | 0.005 | 0.006 | 0.005 | 0.007 |
| Preparation Example 3 | 0.02 | 0.022 | 0.016 | 0.021 |
| Preparation Example 4 | 0.03 | 0.025 | 0.018 | 0.020 |
| Preparation Example 5 | 0.003 | 0.008 | 0.004 | 0.006 |
| Preparation Example 6 | 0.03 | 0.047 | 0.021 | 0.025 |
| Preparation Example 7 | 0.02 | 0.021 | 0.013 | 0.013 |
| Preparation Example 8 | 0.02 | 0.025 | 0.018 | 0.018 |
| Preparation Example 9 | 0.03 | 0.045 | 0.021 | 0.030 |

TEXT EXAMPLE 2

Blood pressure-reducing action

In order to evaluate the blood pressure-reducing action of the present compounds, each of the compounds was dissolved in dimethylsulfoxide and administered intravenously to dogs. After administration, a dose of the compound effective to reduce the blood pressure by 20% (ED$_{20}$:mg/Kg) was measured. The results are shown in Table 2.

TABLE 2

| Compound | ED$_{20}$ (mg/Kg, i.v.) |
|---|---|
| Preparation Example 1 | 1.2 |
| Preparation Example 2 | 1.2 |
| Preparation Example 3 | 0.4 |
| Preparation Example 4 | 0.5 |
| Preparation Example 5 | 1.6 |
| Preparation Example 6 | 1.5 |
| Preparation Example 7 | 1.6 |
| Preparation Example 8 | 1.8 |
| Preparation Example 9 | 1.5 |

TEST EXAMPLE 3

Blood-flow increasing action

In order to evaluate the blood-flow increasing action of the present compounds, each of the compounds was dissolved in dimethylsulfoxide and administered intravenously to dogs. After administration, a dose required to increase the blood-flow in the carotid by 30% was determined. The results are shown in Table 3.

TABLE 3

| Compound | Carotid blood-flow increasing action (ED$_{30}$ μg/Kg, i.v.) |
|---|---|
| Preparation Example 2 | 9.0 |
| Preparation Example 3 | 30.0 |
| Preparation Example 4 | 66.0 |
| Preparation Example 5 | 9.4 |
| Preparation Example 6 | 190.0 |

TEST EXAMPLE 4

Acute toxicity test

Each of the present compounds suspended in a carboxymethyl cellulose was administered orally to a mouse and a 50% lethal dose (LD50) was measured. There was not observed any dead mouse even with the administration as high as 2,000 mg/Kg. The results are shown in Table 4.

TABLE 4

| Compound | LD50 (oral administration to mouse, mg/Kg, i.v.) |
|---|---|
| Preparation Example 5 | 2,000 or more |
| Preparation Example 6 | 2,000 or more |

3. Formulation Examples

FORMULATION EXAMPLE 1

To 10 g of the compound from Preparation Example 2 are added 50 g of lactose, 30 g of potato starch and 20 g of abisel and the mixture is thoroughly blended. Thereto is added 5 ml of a 3% hydroxy-propyl cellulose solution to give granules. The granules are incorporated with 1 g of magnesium stearate and then formed into tablets of 6 mm in diameter according to a conventional method to give 945 pieces of tablets.

FORMULATION EXAMPLE 2

To 20 g of the compound from Preparation Example 6 are added 60 g of lactose, 20 g of potato starch and 15 g of abisel. After sufficient mixing, the mixture is placed in No. 4 capsules according to Pharmacopoei of Japan so that each capsule contains 115 mg of the mixture.

Thus, 920 pieces of capsules are obtained.

What is claimed is:

1. A pyrano[f]quinoline compound of the formula (I):

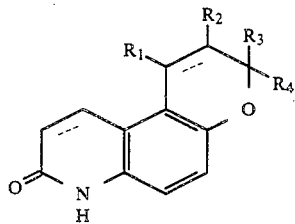

wherein $R_1$ and $R_2$ are identical or different and represent hydrogen, hydroxyl group or a group of the formula:

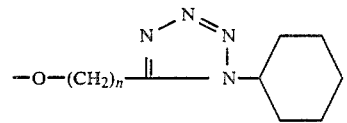

wherein, n represents an integer from 1 to 4, $R_3$ and $R_4$ are identical or different and represent hydrogen or a lower alkyl group having from 1 to 4 carbon atoms, and the broken lines in the rings represent that the bond between the carbon atoms at the 1- and 2-positions and the bond between the carbon atoms at the 9- and 10-positions may be double bonds; excluding the compounds of the formula (I), where $R_1$ and $R_2$ are hydrogen, $R_3$ and $R_4$ are identical or different and represent a lower alkyl, and the bond between the carbon atoms at the 1- and 2-positions and the bond between the carbon atoms at the 9- and 10-positions are both double bonds.

2. A pharmaceutical composition comprising a compound as recited in claim 1 in an amount which is pharmacologically effective as an anti-thrombotic agent, a cerebral circulation improving agent, a hypotensive agent, an anti-angina agent, an anti-asthmatic agent, an anti-ulcer agent or an anti-PAF agent.

3. A pharmaceutical composition as claimed in claim 2 which is an anti-thrombotic agent, platelet aggregation inhibitory agent, cerebral circulation improving agent and/or hypotensive agent.

* * * * *